(12) United States Patent
Blahut

(10) Patent No.: US 6,248,731 B1
(45) Date of Patent: Jun. 19, 2001

(54) STABILIZED ASPIRIN COMPOSITIONS AND METHOD OF PREPARATION FOR ORAL & TOPICAL USE

(76) Inventor: Natalie Blahut, 9302 Miccosukee, Tallahassee, FL (US) 32308

( * ) Notice: Subject to any disclaimer, the term of this patent is extended or adjusted under 35 U.S.C. 154(b) by 0 days.

(21) Appl. No.: 09/739,018

(22) Filed: Dec. 19, 2000

Related U.S. Application Data

(62) Division of application No. 09/518,667, filed on Mar. 3, 2000, now Pat. No. 6,177,413.

(51) Int. Cl.⁷ .................................................. A61K 31/60
(52) U.S. Cl. .............................................................. 514/159
(58) Field of Search ................................................ 514/159

(56) References Cited

U.S. PATENT DOCUMENTS

| | | | |
|---|---|---|---|
| 1,217,862 | 2/1917 | Gerngross et al. | 514/159 |
| 3,279,990 | 10/1966 | Rose et al. | 514/159 |
| 4,228,162 | 10/1980 | Luzzi et al. | 424/232 |
| 4,885,287 | 12/1989 | Hussain et al. | 514/159 |
| 5,723,453 | 3/1998 | Phykitt | 514/165 |

FOREIGN PATENT DOCUMENTS 1489672   10/1977   (GB).

*Primary Examiner*—Raymond Henley, III
(74) *Attorney, Agent, or Firm*—Dowell & Dowell

(57) ABSTRACT

Aspirin compositions for oral and topical use are stabilized by reaction with potassium hydroxide.

9 Claims, No Drawings

STABILIZED ASPIRIN COMPOSITIONS AND METHOD OF PREPARATION FOR ORAL & TOPICAL USE

This is a divisional of U.S. application Ser. No. 09/518,667 filed Mar. 3, 2000, now U.S. Pat. No. 6,177,413.

BACKGROUND OF THE INVENTION

1. Field of the Invention

This invention relates to using potassium hydroxide, KOH, to stabilize acetylsalicylic acid, ASA, salicylic acid, SA, and any other related composition and ascorbic acid for oral and topical use.

2. Discussion of the Related Art

U.S. Pat. No. 1,349,207 to Galat discloses the use of alkaline solvents to stabilize aspirin compositions in solution and describes salicylic acid and acetic acid as undesirable byproducts of the breakdown of acetylsalicylic acid (ASA). To avoid this breakdown of ASA, anionic exchange materials are used. Galat articulates the general assumption that, in order to stabilize aspirin, one must begin with ASA.

Salicylic acid (SA) is closely related to salicin, the earliest form of aspirin found in white willow bark, meadowsweet and other botanicals. American Indian tribes used it in therapeutic baths and teas, as did early Americans. The botanicals are still sold in certain health food stores and used in the same way.

Potassium Hydroxide (KOH) has been used as a stabilizer for Aspirin in Solution. In one patent, KOH was used as a catalyst in the processing of Aspirin. In U.S. Pat. No. 3,279,990 to Rose et al., U.S. Pat. No. 1,217,862, to Gerngross, U.S. Pat. No. 4,228,162, to Luzzi et al., and U.S. Pat. No. 4,885,287, to Hussain et al., sodium hydroxide is used to stabilize an aspirin in solution; however, the high sodium content was, and is, undesirable. In the patent to Luzzi et al., it is noted that the stability of aspirin in a solution increases with increasing concentration of the drug. Using dimethyl isosorbate as a solvent, the patent achieves a concentration of 280 mg of ASA/ml.

In the past, KOH was used to restore electrolytes in animals in veterinary practice. It also is used in solution to saponify vegetable oils in the making of castile soap.

Examination of the properties of ascorbic acid and salicylic acid suggests that the therapeutic action, acidity, antiseptic quality, historical range of uses, and even side effects when separated from its original plant source, as well as the manner in which it deteriorates by esterification, of salicylic acid resembles vitamin C. Also, vitamin C is a detoxifier.

Earlier cultures have used whole plant forms of salicin as a remedy for food poisoning and dysentery, suggesting a possible detoxifying role for SA. Although aspirin, as we know it, may injure the gastrointestinal tract, teas from plants containing salicin were used for healing it.

Studies at Cornell University about how plants create SA which prevents microbes from causing disease in them suggest a unique role for SA, other than as a drug. If SA functions as an agent which combines with excess wastes or undesirable substances, including microbes in the body, and carries them off through circulation without leaving toxic traces of its own, then like ascorbic acid, SA may qualify as a detoxifier. If it is not simply a drug but a detoxifier, its role in health could become therapeutic or healing rather than simply medicinal.

A problem persists, however, in stabilizing solutions of ASA or SA which would allow effective oral and/or topical application of such drugs for either medicinal or therapeutic uses. When mixed in water, such substances rapidly biodegrade and become unsuitable for use.

In view of the foregoing, there remains a need to prolong the stability of an aspirin or aspirin-like product, ASA and SA, in a soluable state in a water base solution for purposes of obtaining a medicinal drug, and possibly a therapeutic detoxifer, which can be administered both orally and topically and which will exhibit a commercially and medically acceptable shelf life.

SUMMARY OF THE INVENTION

Salicylic acid, SA, and Acetylsalicylic Acid, ASA, are dissolved in solutions of potassium hydroxide, KOH, to form potassium salicylic acid (KSA) and potassium acetylsalicyclic acid (KASA). In some embodiments, dehydration shortly after mixing in solution and while the liquid is still hot from its own chemical reaction reduces the biodegradation which sometimes occurs when water is present with SA and ASA.

The more concentrated the KOH solution is, the more SA or ASA that dissolves and the less the chance for degradation. A solution at or close to its saturation point for SA and ASA remains liquid upon cooling. On the other hand, a supersaturated solution remains liquid only while it is still hot and lends itself to rapid dehydration immediately after the solids are thoroughly dissolved. This manner of facilitating the drying process overcomes the problem of SA's and ASA's resistance to giving up moisture in dehydration.

Making a preferably alkaline formula of KSA and KASA at maximum concentration, limited by a desired pH, is desirable and the resultant formula is diluted for use. The pH values should be within optimal range and are related to the body's physiological well-being or the preference or need of different body systems, e.g., the GI tract, the skin.

The pH of an oral formula should be in the range of 8–10. This pH counteracts excess acidity and soothes the gastrointestinal(GI), tract.

Finding a high dose aspirin without GI side effects is probably the main reason why a new more gentle form of aspirin has been sought for nearly a century. The alkaline formulas of the present invention permit higher doses and have powerful yet soothing systemic effects. The importance of this is that many small doses do not achieve the same result as one large dose.

In the preferred embodiment for oral alkaline formulas, approximately two parts by weight SA or ASA is dissolved with one part KOH in a water base KOH solution. The solution chemically reacts until the substances are fully soluabilized as potassium KSA or KASA. A resultant pH of about 12–13 is achieved. For administration, the pH is lowered by diluting the KSA or KASA in water to a pH of between 8 and 10.

In a preferred embodiment for topical application, a water based, preferably aloe vera gel, lotion or cream is mixed and combined with dehydrated KSA. The pH of the resultant topical lotion is approximately 4.62.

In some embodiments the liquid KSA and KASA formulations are rapidly dehydrated by heating before the liquid formulation cools from the initial mixing to thereby reduce biodegration of the resultant anhydrous KSA or KASA. The anhydrous KSA or KASA can subsequently be dissolved in water for oral administration or mixed with a carrier for topical applications.

It is a primary object of the present invention to prolong the stability of an aspirin or aspirin-like product, which stabilized product can be taken orally or applied topically when mixed with a suitable carrier.

It is another primary object of the present invention to provide an aspirin formulation which can be used to permit higher doses of SA and ASA to be administered orally for substantially all known uses of aspirin without the adverse side affects currently present in aspirin products.

It is also an object of the present invention to provide aspirin formulations which may be applied topically to provide treatment and relief from insect bites, bee stings, sores, burns, rashes, itching from poisonous botanicals, funges and the like.

DESCRIPTION OF THE PREFERRED EMBODIMENTS

The present invention is directed to methods of stabilizing aspirin and aspirin-like compounds, ASA and SA, for oral and topical medicinal and therapeutic uses wherein greater doses of ASA and SA can be safely administered for both human as well as animal treatment. In order to prevent degradation of the ASA, SA, it has been determined that these compounds can be chemically reacted with potassium hydroxide, KOH, in proper proportions and under conditions which result in an alkaline pH in the range of 8 to 10 for oral administration and an acid pH between 4–5 for topical administration.

Through testing it has been determined that the concentration of KOH in solution should be as high as possible while still obtaining a complete chemical reaction to convert all ASA or SA to KASA or KSA. A solution which is at or close to its saturation point with respect to the ASA or SA will remain liquid after the reaction with KOH. However, supersaturated solutions are dehyradrated after the solids are initially dissolved to form anhydrous aspirin-like products that readily dissolve in liquid for administration.

EXAMPLE 1
A Supersaturated Oral Alkaline SA Formula

In 50 ml water, 37 gms KOH are mixed with 76 gms SA. The mixture chemically reacts and the solids are soluabilized with solutions resulting in a yield of concentrated KSA of 127 ml. The pH of the concentrated KSA is about 12.0–13.0. The concentration of salicylic acid, SA, is about 600 mg/ml and K is 204 mg/ml. The KSA is then dehydrated, A dosage of 1 gm of dehydrated KSA is mixed with 225 ml water wherein approximately 680 mg SA and 231 mg K are in solution with a pH of 8.90. Administration is by gradual ingestion by sipping. A much higher dose of 2 gm KSA can be administered as needed using two 1 gm doses separated by an interval of time so that the doses overlap closely.

By concentrating a solution of SA and KOH or a solution of ASA and KOH to a point of supersaturation, a rapid dehydration of an anhydrous aspirin-like product may be achieved wherein the product is easily dissolved in water or a water base carrier lotion or cream for use. By way of example, in the method of stabilizing aspirin in a supersaturated solution, the aspirin such as SA is dissolved in a solution of KOH to form potassium salicylic acid (KSA). Dehydration shortly after mixing, while the liquid is still hot from its own chemical reaction reduces the biodegradation which sometimes occurs when water is present with aspirin.

The more concentrated the KOH solution is, the more SA it dissolves and the less the chance for degradation. A solution at or close to its saturation point for SA remains liquid upon cooling. On the other hand, a supersaturated solution remains liquid only while it is still hot and lends itself to rapid dehydration immediately after the solids are thoroughly dissolved. This manner of facilitating the drying process overcomes the problem of aspirin's resistance to giving up its moisture in dehydration.

An Example of supersaturated ASA oral formula is as follows:

EXAMPLE 2
An Alkaline Oral ASA 50 ml water combined with 41 gm KOH and 55 gm preferably sifted ASA to yield 108 ml KASA. The concentration is 510 mg/ml ASA and 383 mg/ml K. The KASA solution is dehydrated. A dosage of 1 gm dehydrated KASA is mixed in 225 ml water wherein, 573 mg ASA and 299 mg K are in solution with a pH of 8.42.

The present invention also uses KSA to provide a low acid topical formula which is very transdermal and delivers aspirin directly to muscles and joints, relieving pain at is locus. Applied even over most of the body, it has a beneficial systemic effect, not unlike the oral formula. A pH of 4 to 5 and preferably 4.5 is used for topical applications because: microbial activity is low at this pH; the pH of normal healthy skin falls in this range; and natural body care products are most likely to fall within this pH range.

An example of a topical KSA is as follows: Using the supersaturated KSA formula of Example 1, a topical formula was prepared as follows: 225 ml Aloe Vera Gel was mixed with 2½ ml liquid castile soap (Dr. Bronner's was used), and 2½ ml vegetable glycerin. Dry ingredients of 900 mg citric acid, 600 mg guar gum and 14 gm dehydrated KSA are separately mixed. The liquid and dry ingredients were subsequently mixed resulting in a pH of 4.62. The KSA topical lotion yields approximately 40.78 mg SA/ml.

The primary advantage of the topical formulas is that they can be applied repeatedly and can be used as a poultice on a wound, burn, area of persistent itching, mosquito or other insect bite, bee stings or areas of pain such as arthritic joints. In this manner, aspirin is continually delivered in small amounts to affected body areas until local symptoms subside.

Any other ingredients compatible with any of the formulas can be added to them for enhancement, such as flavor for the oral formulas or texture, color and such for the topical formula. Peppermint oil enhances the oral formula and is often used to soothe the stomach.

The oral uses for the KSA and KASA formulas allow higher doses to be administered for systemic ailments. While acting on one systemic condition, other symptoms are alleviated, e.g., mild head congestion and pain, including tension, head, ear, jaw and neck pain, minor GI distress, and coughs. Other wide-ranging potential benefits including the possibility of treatment of serious immunological diseases and possible preventive uses. Topical KSA and KASA are used dermatologically for mildly sun-damaged skin, for washing, itching, rashes, insect bites, muscle spasms, cramps, restless legs. The topical formula also has many anecdotals available.

Sometimes when using an oral formula; a localized area may require additional topical relief. A topical application for muscle pain may also benefit from oral systemic relief. This is especially true where an entire body is involved, as in fibromyalgia.

The topical formulas have also been used on animals with severe skin ailments and found to be effective.

The foregoing description of the preferred embodiments of the invention has been presented to illustrate the principles of the invention and not to limit the invention to the particular embodiments disclosed. It is intended that the scope of the invention be defined by all of the embodiments encompassed within the following claims and their equivalents.

What is claimed is:

1. A medicinal drug which is mixed with a liquid carrier for oral or topical application to mammals to treat malodies conventionally treated using aspirin product, said drug being formed by combining a salicylic acid with potassium hydroxide in a water based solution to form potassium salicylic acid which is thereafter dehydrated to form a stabilized dry potassium salicylic acid.

2. The medicinal drug of claim 1 wherein the salicylic acid is combined to a point of supersaturation in the water based solution.

3. The medicinal drug of claim 1 mixed with water to form a dosing solution with a pH in the range of 8 to 10.

4. The medicinal drug of claim 1 mixed with a water based carrier including a dermtologically acceptable lotion, cream, gel or ointment with a resulting pH which is compatible to mammalian skin.

5. The medicinal drug of claim 1 wherein approximately one part by weight potassium hydroxide is combined in the water based solution with two parts by weight salicylic acid.

6. A medicinal drug which is mixed with a liquid carrier for oral application to mammals to treat malodies conventionally treated using aspirin product, said drug being formed by combining a acetylsalicylic acid with potassium hydroxide in a water based solution to form potassium acetylsalicylic acid which is thereafter dehydrated to form a stabilized dry potassium acetylsalicylic acid.

7. The medicinal drug of claim 6 mixed with water to form a dosing solution with a pH in the range of 8 to 10.

8. The medicinal drug of claim 6 mixed with a water based carrier including a dermtologically acceptable lotion, cream, gel or ointment with a resulting pH which is compatible to mammalian skin.

9. The medicinal drug of claim 6 wherein approximately one part by weight potassium hydroxide is combined in the water based solution with two parts by weight acetylsalicylic acid.

* * * * *